United States Patent
Costargent

(10) Patent No.: US 9,445,875 B2
(45) Date of Patent: Sep. 20, 2016

(54) DEVICE FOR HOLDING MEDICAL EQUIPMENT, TREATMENT KIT, AND ASSOCIATED PREPARATION METHOD

(71) Applicant: Alain Pierre Jean Costargent, Nantes (FR)

(72) Inventor: Alain Pierre Jean Costargent, Nantes (FR)

( * ) Notice: Subject to any disclaimer, the term of this patent is extended or adjusted under 35 U.S.C. 154(b) by 67 days.

(21) Appl. No.: 14/398,714

(22) PCT Filed: Apr. 30, 2013

(86) PCT No.: PCT/EP2013/059014
§ 371 (c)(1),
(2) Date: Mar. 20, 2015

(87) PCT Pub. No.: WO2013/164350
PCT Pub. Date: Nov. 7, 2013

(65) Prior Publication Data
US 2015/0250544 A1 Sep. 10, 2015

(30) Foreign Application Priority Data
May 2, 2012 (FR) ..................................... 12 54019

(51) Int. Cl.
| A61M 25/00 | (2006.01) |
| B65D 85/00 | (2006.01) |
| A61B 17/00 | (2006.01) |
| A61B 19/02 | (2006.01) |
| A61M 25/01 | (2006.01) |
| F16L 3/01 | (2006.01) |
| F16L 3/26 | (2006.01) |
| A61M 25/09 | (2006.01) |

(52) U.S. Cl.
CPC ....... *A61B 19/0256* (2013.01); *A61M 25/0111* (2013.01); *F16L 3/01* (2013.01); *F16L 3/26* (2013.01); *A61M 25/09041* (2013.01); *A61M 2025/0056* (2013.01); *Y10T 29/49826* (2015.01)

(58) Field of Classification Search
CPC .......... A61M 25/0111; A61M 25/002; A61M 25/09041; A61B 19/0256; A61B 19/26; B65H 75/36; F16L 3/01; F16L 3/26
USPC ....... 248/49, 50, 51, 68.1, 80, 89, 52, 309.1; 600/104, 102, 153, 171, 180, 250; 206/363, 370, 357, 438; 134/117; 128/852
See application file for complete search history.

(56) References Cited

U.S. PATENT DOCUMENTS

| 3,284,025 A | * | 11/1966 | Fridolph | ................ B65D 59/04 206/0.83 |
| 3,578,777 A | * | 5/1971 | DeGain | .................... F16L 11/15 138/121 |
| 4,502,653 A | * | 3/1985 | Curtis, Jr. | ................. F16L 3/18 248/55 |

(Continued)

FOREIGN PATENT DOCUMENTS

| DE | 2509063 A1 | 9/1976 | |
| DE | 19956480 A1 * | 6/2001 | ........... E04D 13/072 |
| EP | 1145730 A1 | 10/2001 | |

*Primary Examiner* — Tan Le
(74) *Attorney, Agent, or Firm* — Knobbe Martens Olson & Bear LLP

(57) ABSTRACT

A device includes a channel, which defines an inner space for receiving medical equipment. The channel is reversibly deformable between a first stable spatial configuration and at least one second stable spatial configuration. The device includes a plurality of holders for supporting the channel over a bearing surface. The device also includes a distal wall and a proximal wall longitudinally closing off the inner space.

17 Claims, 5 Drawing Sheets

(56) References Cited

U.S. PATENT DOCUMENTS

| | | |
|---|---|---|
| 5,160,559 A | 11/1992 | Scovil et al. |
| 6,375,066 B1* | 4/2002 | Ritter .................. B65D 5/0005 229/101.2 |
| 6,802,323 B1 | 10/2004 | Truwit et al. |
| 2006/0289104 A1* | 12/2006 | Haggerty .................. F16L 7/00 156/60 |
| 2015/0250544 A1* | 9/2015 | Costargent ......... A61M 25/0111 248/49 |

* cited by examiner

DEVICE FOR HOLDING MEDICAL EQUIPMENT, TREATMENT KIT, AND ASSOCIATED PREPARATION METHOD

CROSS-REFERENCE TO RELATED APPLICATIONS

This application is the U.S. National Phase under 35. U.S.C. §371 of International Application PCT/EP2013/059014, filed Apr. 30, 2013, which claims priority to French Patent Application No. 1254019, filed May 2, 2012. The disclosures of the above-described applications are hereby incorporated by reference in their entirety.

The present invention relates to a device for holding medical equipment.

The device according to the invention is particularly suitable for receiving medical equipment with a large length relative to their width.

It is in particular able to receive equipment designed to be inserted into the vascular system of a patient in order to diagnose or treat a pathology. One example of medical equipment that can be inserted consists of a surgical guide, a catheter, an expansion balloon, a device for inserting an implant, such as a stent, an endoprosthesis, a cover stent, a valve, or a device for inserting a probe.

The medical equipment are for example designed to be used in interventional radiology, interventional cardiology, neurosurgery, vascular surgery, heart surgery (percutaneous or transapical valve) or neurovascular procedures (embolization, covered stent).

In order to minimize the interventional risk experienced by the patient, endoluminal techniques for inserting medical equipment through the patient's vascular system are used more and more often.

To that end, a large number of medical equipment can be conducted into the vascular system to a treatment or diagnosis point in the patient's body. The pieces of equipment are inserted into the body by an incision or a percutaneous puncture in an artery or vein, for example, a wrist, or through a femoral route, inside the thigh.

During this operation, the practitioner first makes the incision and inserts a distal part of the medical equipment into the patient's body.

However, by nature, the medical equipment has a significant length, to allow them to be inserted up to the treatment or diagnosis point. Subsequently, the proximal part of the medical equipment remains placed on a surgical site and is inserted into the patient gradually.

The length of the medical equipment may be significant, for example greater than a meter and in particular approximately 1.80 m, or even up to 3.20 m. The medical equipment can also twist or wind, and it is sometimes difficult to keep them linear on the surgical site.

Such a technique is therefore not fully satisfactory. The proximal part of the medical equipment that is designed to be inserted into the body must remain sterile throughout the entire operation. If it is poorly maintained on the operating field, it may fall on the ground or touch a non-sterile part of the surgical site or its perioperative environment, which may cause microbial contamination. Furthermore, medical equipment are generally provided with an anti-adhesive or hydrophilic coating to facilitate appropriate application thereof in the vascular system. In order to guarantee the anti-adhesive or hydrophilic properties, the coating must remain moist, which is difficult to achieve in an operating room.

One aim of the invention is therefore to provide a device that simplifies the handling of medical equipment, before they are inserted into a patient, while preserving the asepsis and properties of that equipment.

To that end, the invention relates to a device at the aforementioned type, characterized in that it comprises:
- a channel defining an inner space for receiving medical equipment, emerging upward, the channel being reversibly deformable between a first stable spatial configuration and at least one second stable spatial configuration;
- a plurality of holders for supporting the channel, designed to support the channel over a bearing surface bearing the device;
- at least one distal wall and at least one proximal wall longitudinally closing off the inner space.

The device according to the invention may comprise one or more of the following features, considered alone or according to any technically possible combination(s):
- the channel is tightly fastened on at least one of said channels holders;
- it includes a proximal holder and a distal holder, the proximal wall being supported by the proximal channel holder and the distal wall being supported by the distal channel holder;
- at least one of said channel holders is removable relative to the channel;
- the or each channel holder comprises a base designed to be placed on a bearing surface and a concave stirrup designed to be engaged on the channel;
- it includes at least one axial retaining member for the medical equipment positioned in the inner space;
- the or each retaining member includes a transverse retaining wall defining at least one notch for receiving equipment;
- the retaining wall is fastened on one of the proximal wall and the distal wall, or is formed by one of the proximal wall and the distal wall;
- it includes a proximal channel holder, a distal channel holder, and at least one intermediate channel holder positioned between the proximal channel holder and the distal channel holder, the channel having separate segments connecting said channel holders in pairs;
- the channel has a variable active length, the channel having transverse folds, advantageously in accordion form;
- it includes means for keeping the medical equipment positioned above the inner space.

The invention also relates to a treatment kit including a holder device and medical equipment received in the inner space of the channel, the medical equipment advantageously being chosen from among a surgical guide, a device for inserting an implant, such as a stent, a probe, a catheter, an endoprosthesis, a heart valve, a covered stent, a filter and/or a coil.

The kit according to the invention may comprise the following feature:
- it includes a moistening and/or lubrication assembly for the medical equipment, positioned in the inner space of the channel.

The invention also relates to a preparation method for medical equipment, before insertion thereof into a patient's body, characterized in that it includes the following steps:
- providing a device as defined above;
- transitioning the device from a first initial configuration to a second stable spatial configuration;

positioning medical equipment in the inner space;
advantageously, positioning a moistening and/or lubrication assembly in the inner space in contact with the medical equipment.

The invention will be better understood upon reading the following description, provided solely as an example, and in reference to the appended drawings, in which.

Figure 1:
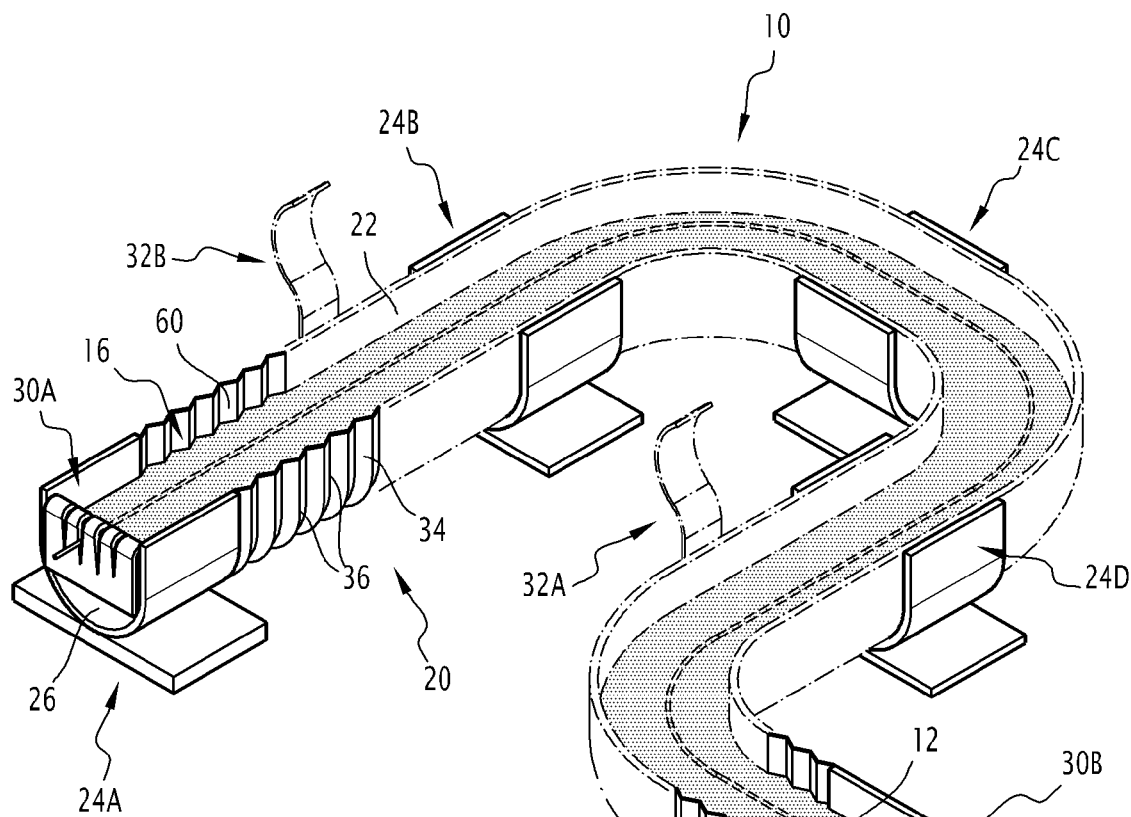
FIG. 1 is a diagrammatic three-quarters front perspective view of a first treatment kit including a holder device according to the invention.
Figure 2:
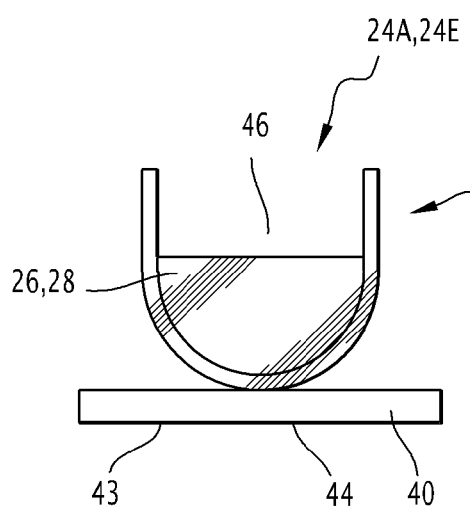
FIG. 2 is a front view of a first channel holder for the device of FIG. 1.
Figure 3:
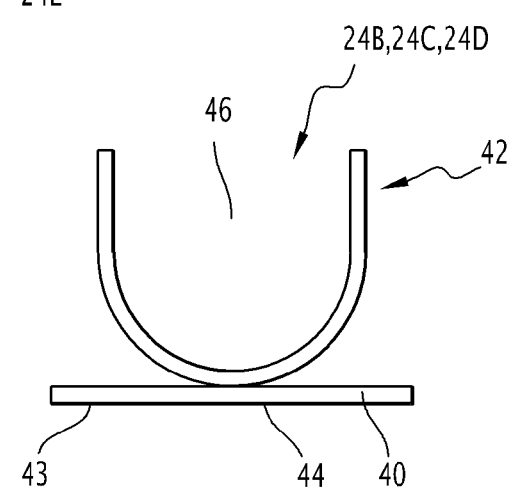
FIG. 3 is a view similar to FIG. 2, for a second channel holder.

A first treatment kit 10 according to the invention is illustrated by FIGS. 1 to 3.

The first kit 10 includes at least one medical equipment 12 designed to be inserted into a patient, and a holder device 14 for the medical equipment 12 designed for packaging and handling of the equipment 12 before it is inserted into the patient and during the insertion. It also includes a moistening and/or lubrication assembly 16 for the medical equipment 12 positioned in the holder device 14.

In this example, the medical equipment 12 has an elongated shape. Its length is much larger than its other dimensions, for example at least two times larger than its other dimensions. The length of the medical equipment 12 may be greater than one meter.

The medical equipment 12 is for example designed to be used in interventional radiology, interventional cardiology, neurosurgery, vascular surgery, heart surgery (percutaneous or transapical valve) and/or neurovascular surgery. It is designed to be inserted into the patient, for example into the patient's vascular system or through another natural conduit, to diagnose and/or treat pathologies.

The medical equipment 12 is in particular chosen from among a guide, a catheter, an expansion balloon, a device for inserting an implant, for example a tubular endoprosthesis, a valve, an endoprosthesis or a covered stent, or a device for inserting a probe.

The medical equipment 12 is designed to be inserted for example using an axillary, subclavian, humeral, radial, femoral, popliteal or leg route.

In the example illustrated in FIG. 1, the equipment 12 is shown by a single filiform line.

As will be seen later, the holder device 14 may contain several different pieces of medical equipment 12, as defined above.

According to the invention, the holder device 14 includes a receiving channel 20 defining an inner space 22 for receiving the medical equipment 12, and a plurality of channel holders 24A to 24E distributed along the length of the channel 20.

The device 14 also includes at least one proximal wall 26 and at least one distal wall 28 longitudinally closing off the inner space 22.

Advantageously, the device 14 further comprises at least one member 30A, 30B for retaining the medical equipment in the inner space 12 and optionally a maintaining member 32A, 32B positioned above the channel 20 (shown in dotted lines in FIG. 1).

As illustrated by FIG. 1, the channel 20 is formed by a half-tube 34 emerging transversely upward relative to a longitudinal axis of the device 14.

The half-tube 34 thus has an upwardly open concave cross-section. This cross-section is for example in the shape of a U or a V.

The channel 20 is longitudinally and transversely deformable in at least two planes, advantageously along three axes.

Thus, the channel 20 can be manipulated manually to go from a configuration with a minimum length to a configuration with a maximum length. Furthermore, the local curvature of the channel 20 can be modified between linear configurations (for example, see FIG. 12) and a plurality of curved configurations (for example, see FIGS. 1, 11 and 13), based on the usage constraints of the equipment 12.

This deformable nature of the channel 20 is provided without any significant plastic deformation. It makes it possible to obtain a plurality of stable configurations of the channel 20, advantageously with no elastic return toward another configuration.

To ensure the deformable nature of the channel 20, in one advantageous embodiment the half-tube 34 includes a plurality of transverse folds 36 extending along a cross-section perpendicular to a local longitudinal axis of the channel 20.

The half-tube 34 thus has an accordion structure, which can be folded and contracted to reduce its length, or contrariwise unfolded and deployed to increase the length and/or modify its curvature.

The minimum length of the channel 20 is for example less than 80% of its maximum length. The minimum length of the channel is for example comprised between 15 cm and 50 cm, and its maximum length is for example comprised between 200 cm and 300 cm.

Advantageously, the width of the channel 20, considered perpendicular to a longitudinal axis of the channel 20, is comprised between 5 cm and 15 cm. The distance separating two consecutive transverse folds 36 is comprised between 2 mm and 30 mm.

The channel 20 is sealed against liquids. To that end, a wall forming the half-tube 34 can retain a liquid in the inner space 22.

Advantageously, the half-tube 34 forming a channel 20 is made from a plastic material, such as a polyolefin, in particular polypropylene, or PVC. Alternatively, the half-tube 34 is formed from a fabric provided with tighten impervious coating.

The inner space 22 is defined laterally and downwardly by the channel 20 and/or locally by the channel holders 24A to 24E.

The inner space 22 emerges upward, advantageously over the entire length of the channel 20, to allow the insertion and removal of medical equipment 12 in the inner space 22.

In the example shown in FIG. 1, the inner space 22 extends continuously over the entire length of the device 14. It is transversely closed off at the ends of the device 14 by the proximal wall 26 and the distal wall 28.

The dimensions of the channel 20 and the inner space 22 therefore make it possible to house different medical equipment based on the dimensions of the equipment.

In the example illustrated in FIG. 1, the holder device 14 includes a proximal holder 24A secured to a proximal end of the channel 20, a distal holder 24E secured to a distal end of the channel 20, and at least one intermediate holder 24B to 24D engaged below the channel 20 between the proximal holder 24A and the distal holder 24E.

The holders 24A to 24E are spaced longitudinally away from each other. They define free segments 35 of the channel 20 between them.

As illustrated by FIGS. 2 and 3, each channel holder 24A to 24E includes a bearing base 40 on a support surface designed to support the device 14, and a stirrup 42 protruding relative to the base 40 to be engaged on the channel 20.

Each holder 24A to 24E is made from a material more rigid than the channel 20.

In the example illustrated in FIGS. 2 and 3, the base 40 and the stirrup 42 are integral. Alternatively, they are made by assembling parts.

As illustrated in FIG. 2, the base 40 advantageously has a planar lower surface 43. It is for example formed by a support plate designed to bear on a planar panel.

The lower surface 43 is advantageously provided with releasable catching means 44 on the support surface designed to support the device 14. The catching means 44 are for example formed by an adhesive, a ferromagnetic element such as a magnet, a snapping device and/or a catching strip such as Velcro.

Thus, each channel holder 24A to 24E can be locally immobilized on the support surface by the catching means 44 to keep the channel 20 in a given configuration.

The stirrup 42 has a convex shape and a cross-section similar to that of the channel 20.

In the example shown in FIG. 1, the holders 24A to 24E situated at the ends of the channel 20 are tightly fastened on the channel 20. Each holder 24A, 24E defines an inner cavity 46 forming a longitudinal part of the inner space 22.

Advantageously, a transverse end edge of the channel 20 is fastened on a transverse end edge of the stirrup 42 at each end holder 24A, 24E.

In the example shown in FIG. 1, at least one intermediate holder 24B to 24D, advantageously all of the intermediate holders 24B to 24D, are removable relative to the channel 20. They are thus able to be assembled and disassembled reversibly and manually by a user, without using an assembly tool.

In this example, each intermediate holder 24B to 24D receives a segment of the channel 20 in the inner cavity 46, over the entire length of the holder 24B to 24D. The stirrup 42 is thus engaged around the end surface of the half-tube 34, outside the inner space 22.

Figure 9:
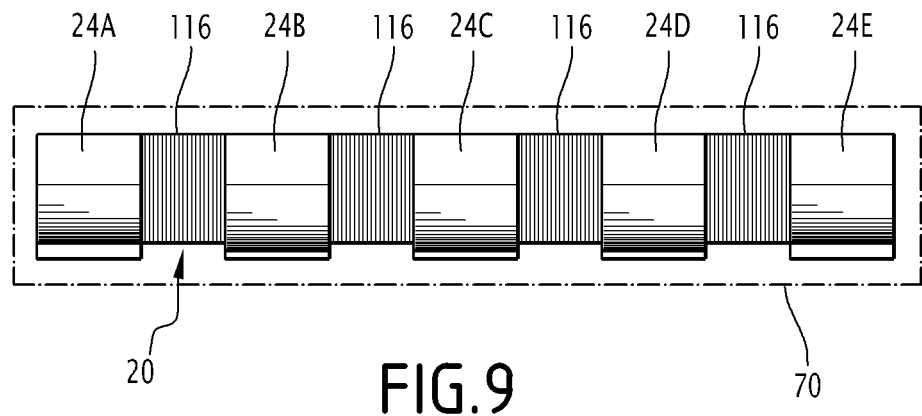
FIG. 9 is a side view of a second holder device according to the invention.
Figure 10:
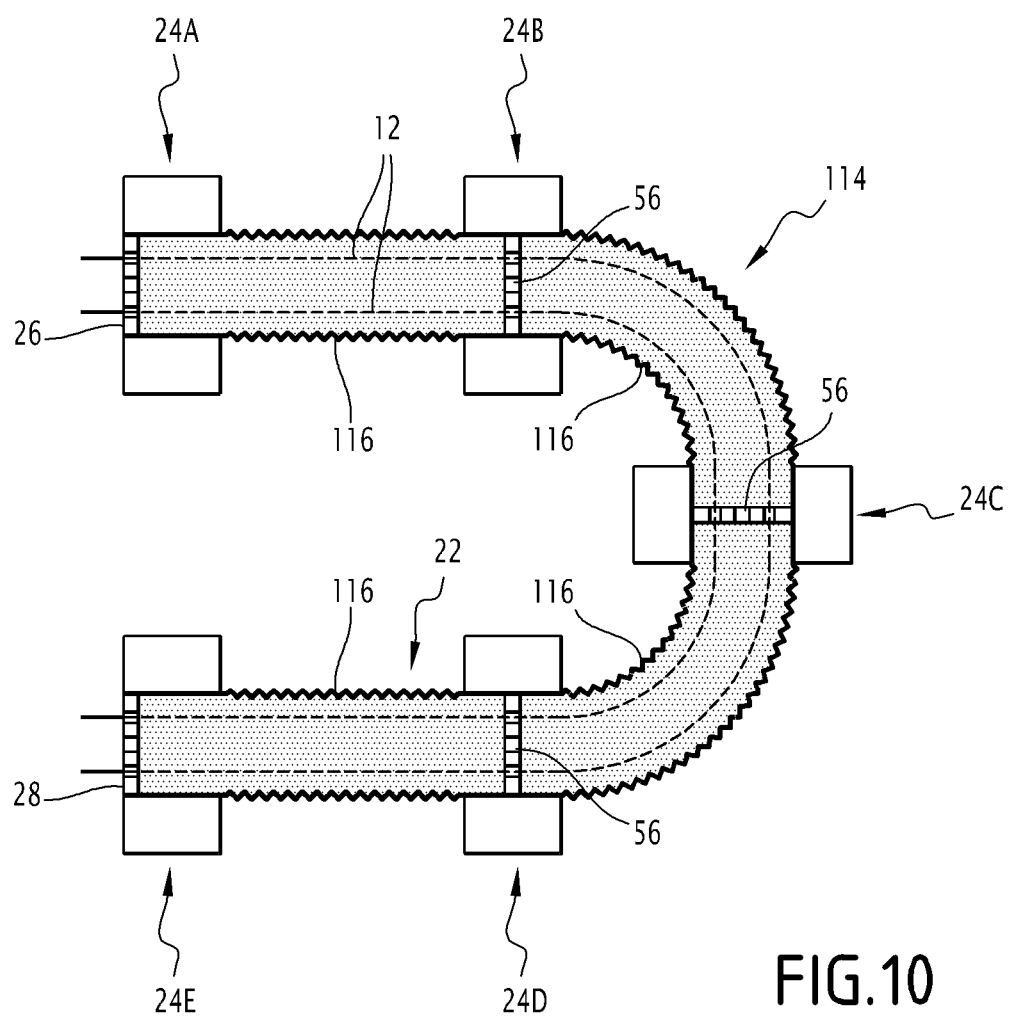
FIG. 10 is a top view of the holder device of FIG. 9 in a usage configuration.

Alternatively, in the device 114 shown in FIGS. 9 and 10, at least one intermediate stirrup 24B to 24D, advantageously all of the intermediate stirrups 24B to 24D, are interposed between two successive segments 35, such that their inner cavity 46 defines part of the inner space 22.

In the example illustrated in FIGS. 1 and 2, the proximal wall 26 and the distal wall 28 are respectively secured to the proximal holder 24A and the distal holder 24E. Each wall 26, 28 extends transversely in the cavity 46 defined by the holder 24A to 24E to close off the inner space 22 transversely.

The height of each wall 26, 28 is advantageously smaller than the height of the stirrup 42.

Thus, the medical equipment 12 and the moistening and lubrication assembly 16 can be retained tightly in the bottom of the inner space 22.

As illustrated by FIG. 1, the device 14 comprises at least one retaining member 30A, 30B for the medical equipment, advantageously a plurality of retaining members 30A, 30B.

In this example, each retaining member 30A, 30B is formed by a staple 50 engaged on one of the proximal wall 26 and the distal wall 28.

Figures 4, 5:
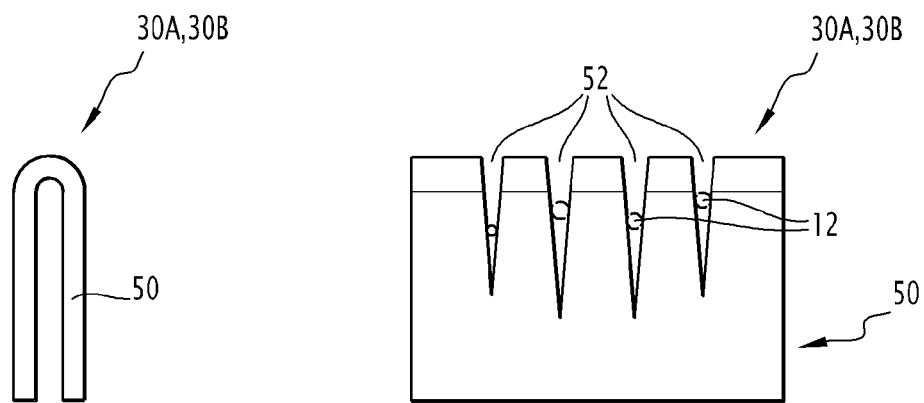
FIG. 4 is a side view of a staple designed to form a retaining member for the medical equipment.
FIG. 5 is a front view of a first alternative of the staple of FIG. 4.

In the example shown in FIG. 5, the staple 50 includes a transverse wall 56 defining at least one notch 52, advantageously a plurality of notches 52, defining a housing for receiving and gripping medical equipment 12.

In the example illustrated in FIG. 5, each notch 52 has a decreasing transverse expanse from top to bottom. Thus, irrespective of the size of the medical equipment 12 inserted into the notch 52, at a given height, the medical equipment may be gripped between the edges of the notch 52 to ensure axial retention.

Figures 6, 7:
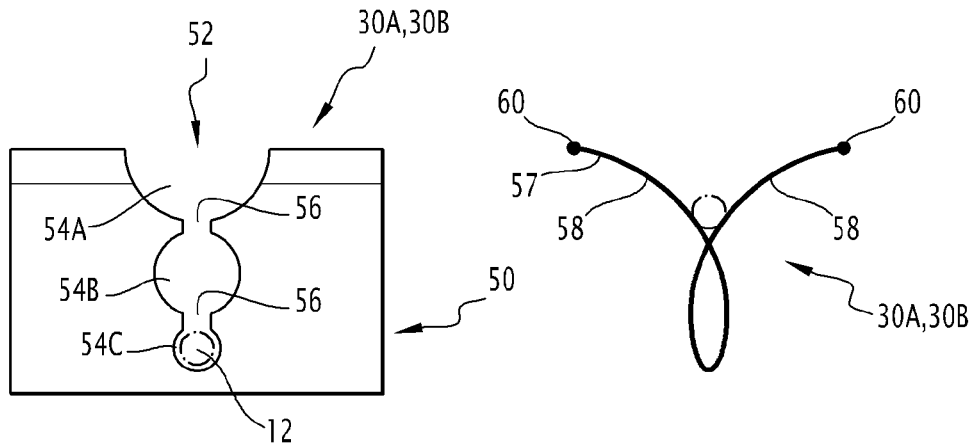
FIG. 6 is a view similar to FIG. 5 of a second alternative of the staple of FIG. 4.
FIG. 7 is a diagrammatic view of a retaining member for the medical equipment.

Alternatively, as illustrated by FIG. 6, at least one notch 52 has a plurality of successive housings 54A, 54B, 54C with decreasing successive transverse dimensions. The housings 54A, 54B, 54C are separated by constrictions 56 retaining the equipment 12 interposed between each pair of adjacent housings 54A to 54C along the notch 52.

Based on its transverse expanse, the medical equipment 12 is selectively inserted into one of the housings 54A to 54C and is retained by the upper constriction 56 situated above the housing 54A to 54C.

Figure 8:
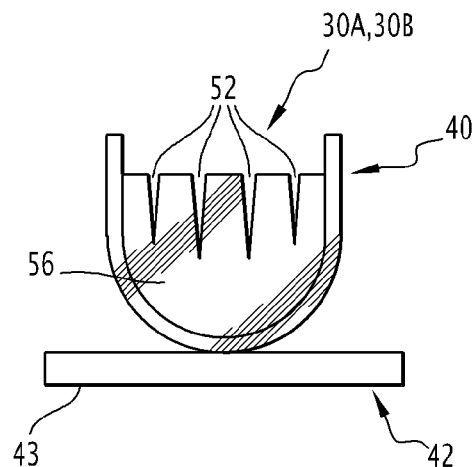
FIG. 8 is a view similar to FIG. 2 of an alternative staple including a retaining member for the medical equipment.

In one alternative shown in FIG. 8, the retaining member 30A, 30B is formed directly in a transverse wall 56 secured to a holder 24A to 24D. It is for example formed in one and/or the other of the proximal wall 26 and the distal wall 28. The notches 52 are then formed directly through the wall 56.

In another alternative shown in FIG. 7, the retaining member 30A, 30B is formed by an elastic member 57, for example filiform and in particular in a loop. In this case, the elastic member 57 assumes the form of a gamma.

The medical equipment 12 is thus able to be received and gripped between two segments 58 of the elastic member 57.

The elastic member 57 is also transversely fastened at its ends 60 on a holder 24A, 24E.

Each retaining member 30A, 30B is thus able to immobilize at least one medical equipment 12 longitudinally to block it longitudinally when the medical equipment 12 is engaged in the retaining member 30A, 30B.

The retaining member 30A, 30B can also release the medical equipment 12 when it must be removed outside the inner volume 22, for example so that it may be inserted into a patient's body.

The maintaining member 32A, 32B is designed to cover the inner space 22 above the channel 20 at least partially, so as to prevent any untimely exit of the medical equipment 12.

In the example shown in FIG. 1, the device 14 includes a plurality of maintaining members 32A, 32B spaced along the channel 20.

Each maintaining member 32A, 32B is for example formed by a strap having one end fastened on a first lateral edge of the channel 20 and one free end able to be fastened on a second opposite lateral edge of the channel 20 to overlap the inner space 22.

The moistening and/or lubrication assembly 16 is for example formed by a liquid 70, such as water or a physiological serum. Alternatively, the assembly 14 includes a spongy material (not shown) retaining the liquid 70 in the bottom of the inner space 22. The spongy material is for example a compress or a sponge.

The medical equipment 12 is thus able to be kept in the liquid 70 or at least in contact therewith.

The channel 20 and the device 14 can be deployed between at least one contracted configuration and a plurality of stable deployed configurations.

In the contracted configuration, the channel 20 is folded and contracted to bring the proximal support 24A close to the distal support 24E. The length of the channel 20 is then minimal.

The intermediate holders 24B to 24D are brought closer to each other and are positioned between contracted free segments 35 of the channel 20.

The length of the device 14 is then minimal. The device 14 can for example be stored in a package 70 such as a box.

In each deployed configuration, the end holders 24A, 24E have been moved away from each other. The length of the channel 20 and the device 14 has been increased.

Figure 11:
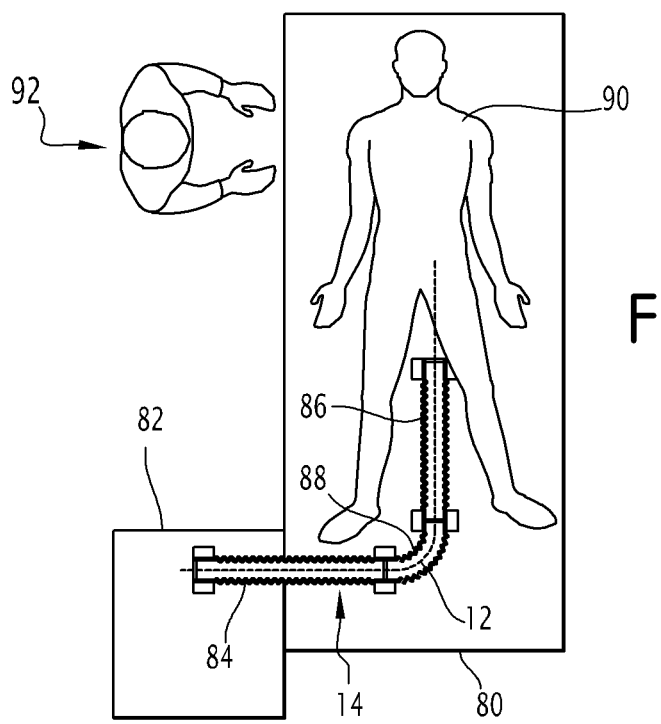
FIG. 11 is a diagrammatic top view illustrating the use of the support device in an operating room, for the insertion of medical equipment via the retrograde femoral route.
Figure 12:
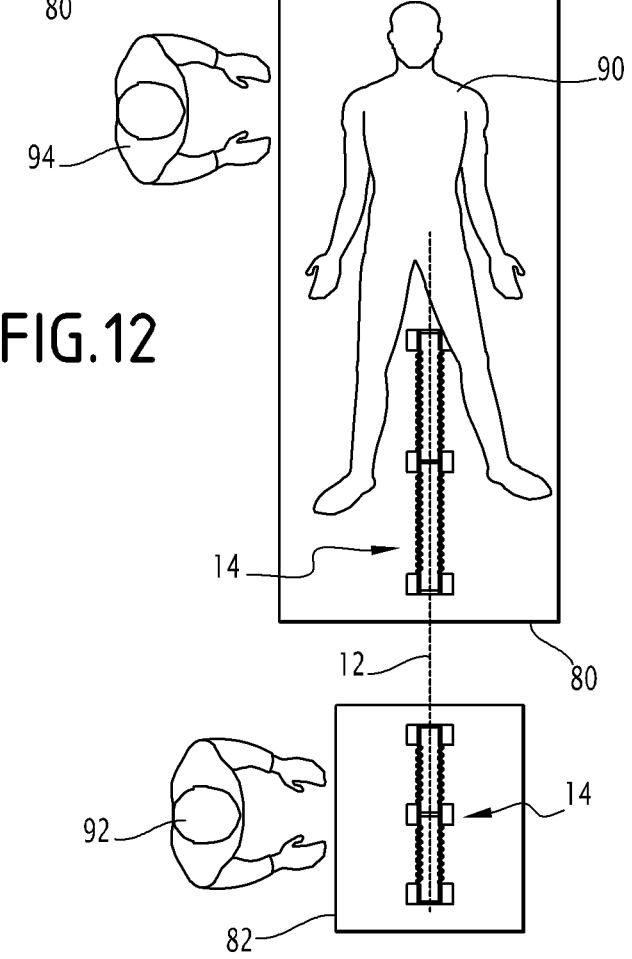
FIG. 12 is a view similar to FIG. 11, illustrating an insertion through the retrograde femoral route with two operators.

In reference to FIGS. 11 to 14, the device 14 can occupy at least one stable linear deployed configuration, as illustrated in FIG. 12, or left or right deployed configurations having bends, as shown in FIGS. 1, 11, 13 and 14.

This makes it possible to adapt to various shapes of medical equipment 12, and various configurations based on the implantation route(s).

A preparation method for a medical equipment 12 using the device 14 according to the invention will now be described.

Initially, the device 14 is provided. When at least one of the holders 24B to 24D is removable, the user removes the device 14 from its package 70, and at least partially deploys the channel 20 in the desired configuration.

The user next engages each intermediate holder 24B to 24D below the channel 20 by moving them away from each other along the channel 20. This provides stable maintenance of the channel 20 in the selected configuration. Advantageously, the user fastens the bases 40 against the support surface supporting the device 14 using fastening means 44.

Then, the user inserts the moistening and/or lubrication assembly 16 into the holder 22, either by pouring liquid 70, or by inserting a spongy material filled with liquid 70.

The user then places the medical equipment 12 in the inner space 22. Advantageously, the medical equipment 12 is axially immobilized in at least one of the retaining members 30A, 30B, for example by engagement in a notch 52 or in an elastic member 57.

The medical equipment 12 is therefore prepared and packaged so that the practitioner can implant it in the patient.

Once the medical equipment 12 is prepared, a method for implanting the equipment may be carried out. To that end, the practitioner removes at least a distal part of the medical equipment 12 from the inner space 22 and inserts it into the patient.

The proximal part of the equipment 12 that is not inserted into the patient, however, remains housed in the inner space 22 of the holder device 14, in contact with the moistening and/or lubrication assembly 16. This limits the risk of microbial contamination or asepsis breaches and keeps the medical equipment 12 under good operating conditions for its implantation.

The presence of the rigid holders 24A to 24E, advantageously fastened on a support surface of the device 14, guarantees that the medical equipment 12 keeps a suitable configuration during its use.

Given that the channel 20 is easily deformable, the device 14 can adapt to different usage configurations, as shown in FIGS. 11 to 14.

Thus, in the example shown in FIG. 11, the device 14 is positioned partially on a support surface defined by an operating table 80 and partially by a secondary table 82 adjacent to the operating table 80.

The device 14 is placed in a configuration comprising a distal linear segment 84 that is perpendicular or inclined relative to the longitudinal axis A-A' of the patient on the operating table 80, and a proximal segment 86 that is substantially parallel to the longitudinal axis A-A' of the patient, the two segments 84 and 86 being separated by a bent segment 88.

Such a configuration of the device 14 for example allows a single operator 92 to insert medical equipment 12 into a patient 90 using the retrograde femoral route.

In the alternative shown in FIG. 12, a first holder device 14 is placed in a linear configuration, substantially parallel to the axis A-A' of the patient on the operating table 80, while being partially inserted between the patient's legs. A second holder device 14 is positioned linearly in the axial extension of the first device 14 on a secondary table 82 positioned in the axial extension of the operating table 80.

The medical equipment 12 can thus be manipulated by a second operator 92 situated across from the secondary table 82, before being inserted into the device 14 situated on the operating table 80 to be manipulated by the practitioner 90.

Such a configuration is therefore suitable for two operators to insert the medical equipment 12 using the retrograde femoral route.

Figure 13:
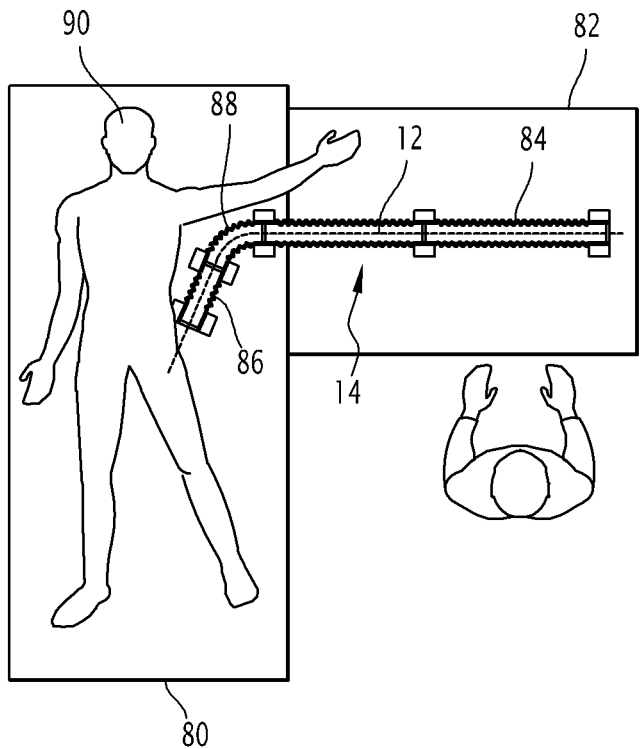
FIG. 13 is a view similar to FIG. 11, illustrating an insertion through the subclavian, axillary, humeral or radial route.

In the example illustrated in FIG. 13, the device 14 comprises a proximal segment 84 placed on a secondary table 82 positioned substantially perpendicular to a longitudinal axis A-A' of the patient on the operating table 80.

The secondary table 82 is placed approximately between an upper limb and a lower limb of the patient.

The proximal segment 86 is placed parallel to the axis A-A' of the patient. The device 14 thus has a bent segment 88 between the distal segment 84 and the proximal segment 86. The device 14 is then particularly suitable for anterograde femoral route insertion of the medical equipment 12 into the patient 90.

Figure 14:
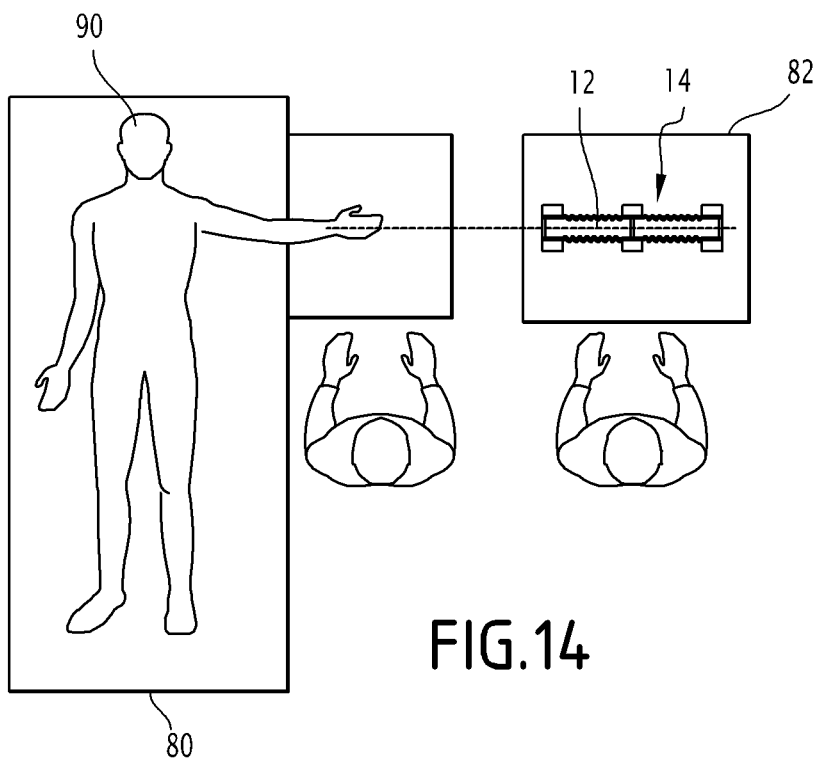
FIG. 14 is a view similar to FIG. 11, illustrating the use of the holder device during insertion through an anterograde femoral route.

In the alternative shown in FIG. 14, at least one holder device 14 is positioned linearly on a secondary table 82, perpendicular to a longitudinal axis A-A' of the patient, and at least one holder device 14 is positioned on the support table 80 with a proximal segment 84 in the axis of the patient and a distal segment 86 substantially perpendicular to the axis of the patient.

This device is suitable for insertion through an upper limb route.

A second device 114 according to the invention is illustrated by FIG. 10. Unlike the first device 14 shown in FIG. 1, the holders 24A to 24E are all secured to the channel 20. Their cavities 46 each define part of the inner space 22.

Thus, each holder 24A, 24E is connected to another holder 24A to 24E by a segment 116 of the channel 20, the channel 20 being interrupted between its different segments 116.

Each intermediate holder 24B to 24D is advantageously provided with a transverse wall 56 able to support a retaining member 30A, 30B, or forming a retaining member 30A, 30B.

The operation of the second device 114 is also similar to that of the first device 14.

In another alternative that is not shown, the proximal wall 26 and the distal wall 28 are formed directly in the channel 20. The holders 24A, 24B then receive, in their inner cavity 46, the end of the channel 20, provided with the proximal wall 26 and the distal wall 28.

The device according to the invention 14, 114 therefore makes it possible to package medical equipment 12 in an operating room, while keeping that medical equipment 12 in a chosen spatial configuration, while preserving the asepsis and maintaining the usage properties of the equipment.

The device 14, 114 according to the invention is particularly easy to use and adapts easily to different techniques for inserting medical equipment into a patient and/or to different types of equipment 12.

What is claimed is:

1. A device for holding medical equipment, comprising:
   a channel defining an inner space for receiving medical equipment, the inner space emerging upward, the channel being reversibly deformable between a first stable spatial configuration and at least one second stable spatial configuration;
   a plurality of holders for supporting the channel, designed to support the channel over a bearing surface bearing the device;
   at least one distal wall and at least one proximal wall longitudinally closing off the inner space.

2. The device according to claim 1, wherein the channel is tightly fastened on at least one of said channels holders.

3. The device according to claim 1, including a proximal holder and a distal holder, the proximal wall being supported by the proximal channel holder and the distal wall being supported by the distal channel holder.

4. The device according to claim 1, wherein at least one of said channel holders is removable relative to the channel.

5. The device according to claim 1, wherein the or each channel holder comprises a base designed to be placed on a bearing surface and a concave stirrup designed to be engaged on the channel.

6. The device according to claim 1, including at least one axial retaining member for the medical equipment positioned in the inner space.

7. The device according to claim 6, wherein the or each retaining member includes a transverse retaining wall defining at least one notch for receiving equipment.

8. The device according to claim 7, wherein the retaining wall is fastened on one of the proximal wall and the distal wall, or is formed by one of the proximal wall and the distal wall.

9. The device according to claim 1, including a proximal channel holder, a distal channel holder, and at least one intermediate channel holder positioned between the proximal channel holder and the distal channel holder, the channel having separate segments connecting said channel holders in pairs.

10. The device according to claim 1, wherein the channel has a variable active length, the channel having transverse folds.

11. The device according to claim 1, including an element for keeping the medical equipment positioned above the inner space.

12. A treatment kit including a holder device according to claim 1 and medical equipment received in the inner space of the channel.

13. The kit according to claim 12, including a moistening and/or lubrication assembly for the medical equipment, positioned in the inner space of the channel.

14. A preparation method for medical equipment, before insertion thereof into a patient's body, including the following steps:
   providing a device according to claim 1;
      transitioning the device from a first initial configuration to a second stable spatial configuration;
   positioning medical equipment in the inner space.

15. The device according to claim 10, wherein the transverse folds of the channel are in accordion form.

16. The kit according to claim 12, wherein the medical equipment is chosen among a surgical guide, and a device for inserting an implant chosen among a stent, a probe, a catheter, an endoprosthesis, a heart valve, a covered stent, a filter and/or a coil.

17. The method according to claim 14, comprising positioning a moistening and/or lubrication assembly in the inner space in contact with the medical equipment.

* * * * *